United States Patent
Mori

(10) Patent No.: US 9,326,729 B2
(45) Date of Patent: May 3, 2016

(54) ELECTRODE CATHETER AND METHOD FOR MANUFACTURING THE SAME

(71) Applicant: Japan Lifeline Co., Ltd., Tokyo (JP)

(72) Inventor: Kenji Mori, Tokyo (JP)

(73) Assignee: Japan Lifeline Co., Ltd., Tokyo (JP)

(*) Notice: Subject to any disclaimer, the term of this patent is extended or adjusted under 35 U.S.C. 154(b) by 0 days.

(21) Appl. No.: 14/415,424

(22) PCT Filed: Mar. 26, 2013

(86) PCT No.: PCT/JP2013/058879
§ 371 (c)(1),
(2) Date: Jan. 16, 2015

(87) PCT Pub. No.: WO2014/013757
PCT Pub. Date: Jan. 23, 2014

(65) Prior Publication Data
US 2015/0190092 A1    Jul. 9, 2015

(30) Foreign Application Priority Data
Jul. 20, 2012 (JP) ................................ 2012-161988

(51) Int. Cl.
| | | |
|---|---|---|
| *A61B 5/04* | (2006.01) | |
| *A61N 1/05* | (2006.01) | |
| *A61B 5/00* | (2006.01) | |
| *A61B 5/042* | (2006.01) | |
| *B32B 37/14* | (2006.01) | |
| *B32B 38/00* | (2006.01) | |
| *A61M 25/00* | (2006.01) | |

(52) U.S. Cl.
CPC ............... *A61B 5/6852* (2013.01); *A61B 5/042* (2013.01); *A61N 1/056* (2013.01); *B32B 37/142* (2013.01);
(Continued)

(58) Field of Classification Search
CPC .............. A61B 5/6852; A61B 5/6869–5/6876; A61B 2562/12; A61B 2562/125; A61B 2562/187; A61B 2562/22; A61B 2562/225; A61B 2562/0209; A61N 1/056; B32B 37/142; B32B 38/0012; B32B 2457/00; B32B 2535/00
USPC ..................................... 600/373, 374; 29/825
See application file for complete search history.

(56) References Cited

U.S. PATENT DOCUMENTS

| 5,257,451 A | * | 11/1993 | Edwards | ........... A61M 25/0138 156/85 |
| 5,524,337 A | * | 6/1996 | Houser | ............. A61M 25/0009 156/86 |

(Continued)

FOREIGN PATENT DOCUMENTS

| JP | H08-000733 | 1/1996 |
| JP | H08-215312 | 8/1996 |

(Continued)

OTHER PUBLICATIONS

English version of International Search Report issued by Japanese Patent Office for the counterpart International application.

*Primary Examiner* — Lee S Cohen
*Assistant Examiner* — Erin M Cardinal
(74) *Attorney, Agent, or Firm* — Muramatsu & Associates

(57) ABSTRACT

An electrode catheter is provided with a catheter shaft (10), an operating handle (20) provided with a connector (70), a tip electrode (31), ring-shaped electrodes (32 to 34), lead wires (41 to 44) connected to the tip electrode (31) and the ring-shaped electrodes (32 to 34), respectively, and a pull wire (50) fixed to the tip electrode (31). The catheter shaft (10) is constituted of a shaft proximal end portion (11) formed of a metal tube having a spiral slit (115) formed in a tip portion, a shaft distal end portion (12) formed of a resin tube of multi-lumen structure, and a resin covering layer (13) covering outer peripheries of the shaft proximal end portion (11) and a rear end portion of the shaft distal end portion (12). The lead wires (41 to 44) and the pull wire (50) extend through different lumens of the resin tube constituting the shaft distal end portion (12). This electrode catheter can exhibit good kink resistance, torque transmissibility and pushability in the entire shaft.

6 Claims, 13 Drawing Sheets

(52) U.S. Cl.
CPC ........... *B32B 38/0012* (2013.01); *A61B 5/6869* (2013.01); *A61B 5/6876* (2013.01); *A61B 2562/0209* (2013.01); *A61B 2562/12* (2013.01); *A61B 2562/222* (2013.01); *A61M 25/0012* (2013.01); *A61M 25/0013* (2013.01); *B32B 2457/00* (2013.01); *B32B 2535/00* (2013.01)

(56) References Cited

U.S. PATENT DOCUMENTS

| | | | | |
|---|---|---|---|---|
| 5,569,200 | A | * | 10/1996 | Umeno ............. A61M 25/0045 604/102.02 |
| 5,755,687 | A | * | 5/1998 | Donlon ............ A61B 17/12022 600/18 |
| 2006/0135961 | A1 | * | 6/2006 | Rosenman ........ A61M 25/0045 606/108 |
| 2010/0217184 | A1 | * | 8/2010 | Koblish ............ A61M 25/0141 604/95.01 |
| 2011/0077498 | A1 | * | 3/2011 | McDaniel .......... A61B 18/1492 600/374 |

FOREIGN PATENT DOCUMENTS

| | | |
|---|---|---|
| JP | 2002-301161 | 10/2002 |
| JP | 2008-245767 | 10/2008 |
| JP | 2011-072782 | 4/2011 |
| JP | 2012-045043 | 3/2012 |

* cited by examiner

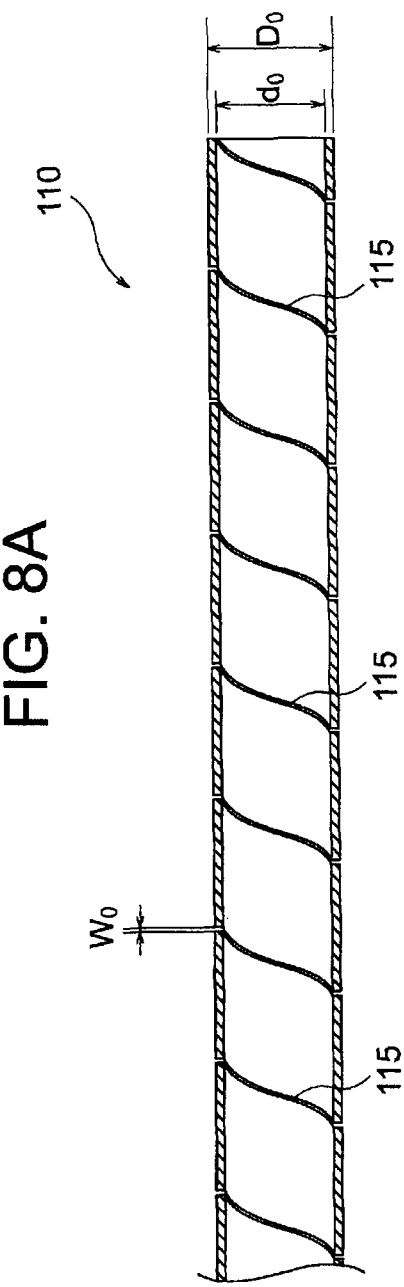
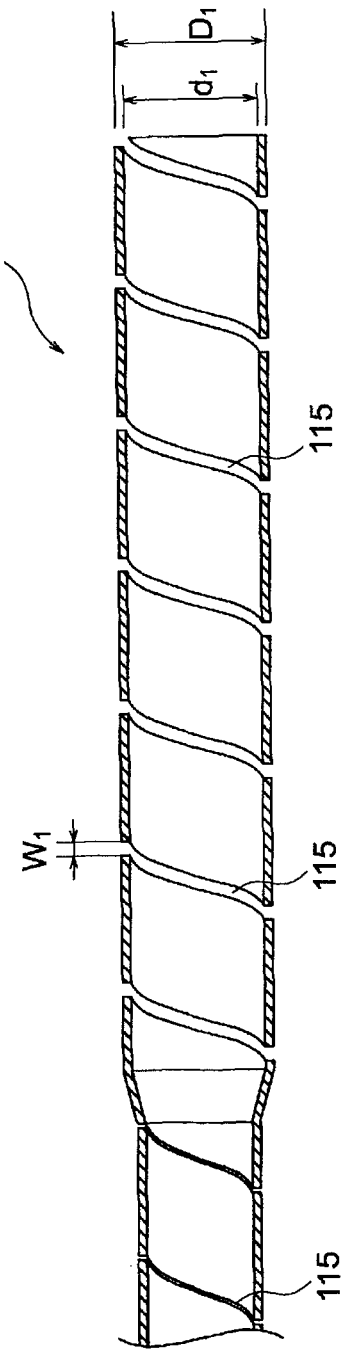
FIG. 8A
FIG. 8B

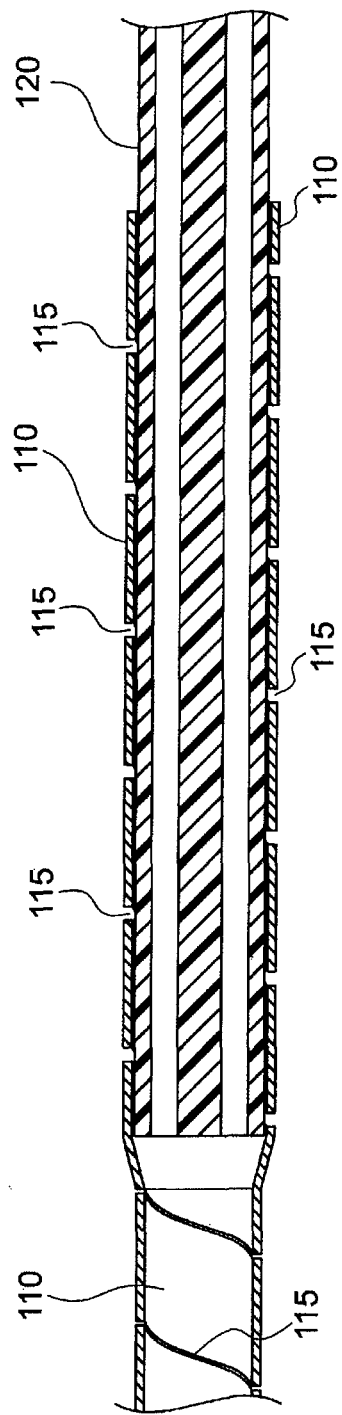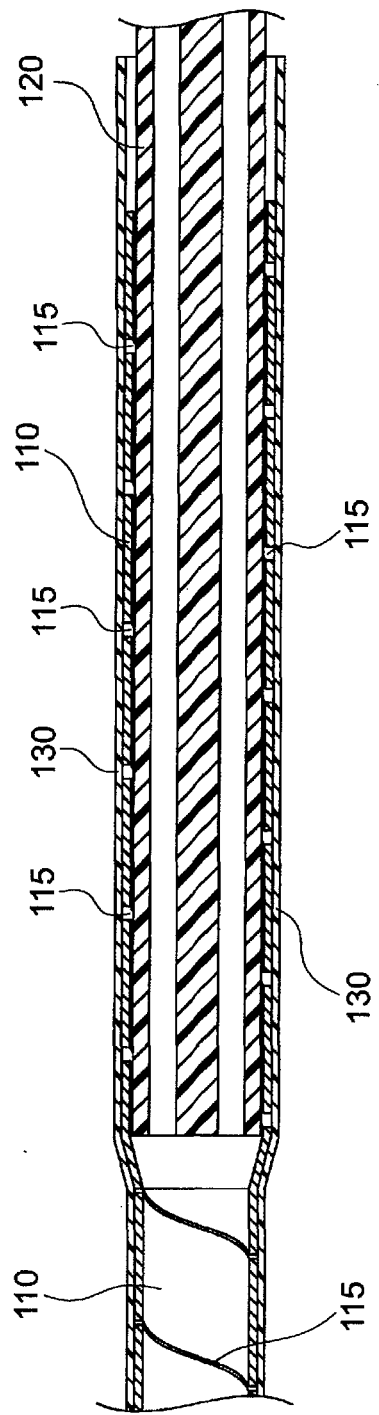

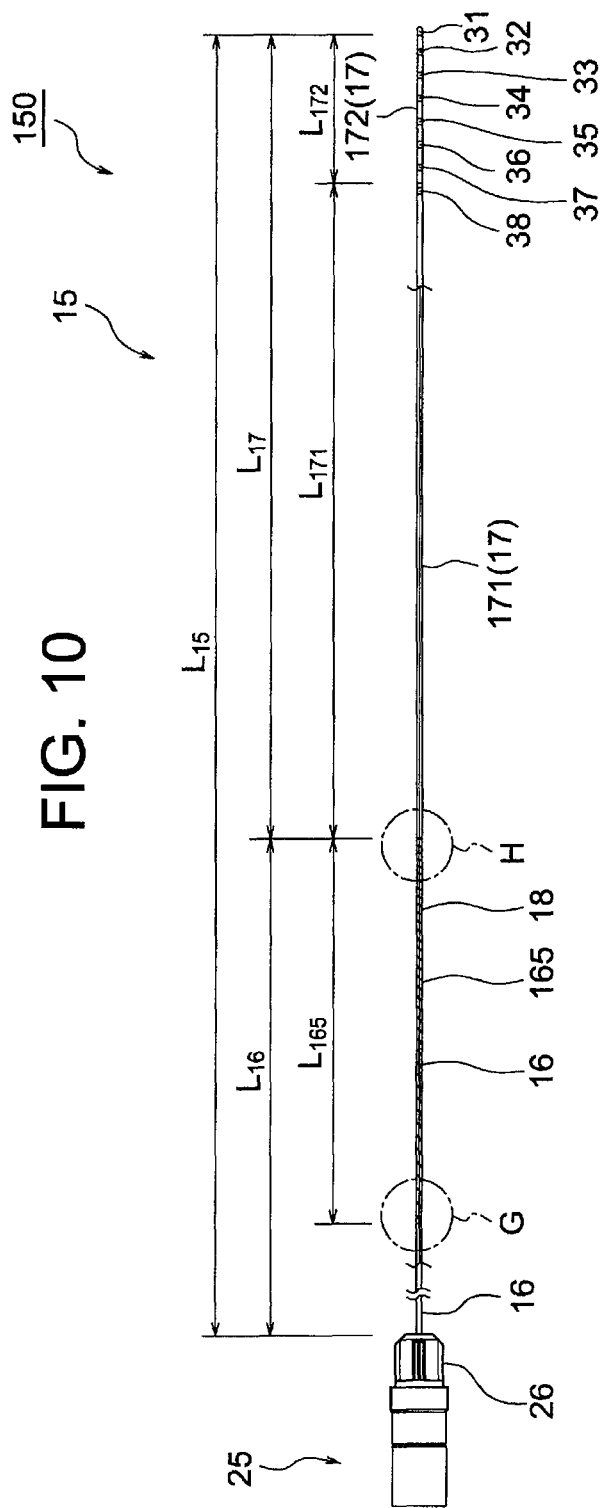

ELECTRODE CATHETER AND METHOD FOR MANUFACTURING THE SAME

This application is a national stage of International Application No. PCT/JP2013/058879 filed Mar. 26, 2013, which claims the benefit of foreign filing based on Japanese Patent Application No. 2012-161988 filed Jul. 20, 2012, the entire contents of which are incorporated herein by reference.

TECHNICAL FIELD

The present invention relates to an electrode catheter provided with a tip electrode.

BACKGROUND ART

Electrode catheters are known as medical devices used for diagnosing or treating irregular heartbeats of heart.

As an electrode catheter for measuring potential in a portion such as a pulmonary vein of heart, the present applicant has proposed an electrode catheter having a catheter shaft, an operating handle connected to a base end side of the catheter shaft, a catheter tip part formed in a circular loop shape connected to a tip side of the catheter shaft, plural ring-shaped electrodes attached to an outer periphery of the catheter tip part, and a tip electrode attached to a tip of the catheter tip side (see Patent Document 1).

The catheter shaft (catheter main body) constituting the electrode catheter described in Patent Document 1 has a single lumen structure (thin long tubular structure having one internal hole) having a resin tube (first tube) with relatively high rigidity and a soft resin tube (second tube) with relatively low rigidity.

Here, a preferred outside diameter of the catheter shaft is 2.3 to 2.4 mm (see [0021] to [0025] of Patent Document 1).

Thus, for example, when plural (for example, two to three) electrode catheters are passed through one sheath and inserted into a heart so as to measure intracardiac potentials simultaneously in plural regions, the outside diameter of the catheter shaft constituting these catheters is desirably smaller than an outside diameter which is preferred in Patent Document 1 (for example, 1.4 mm or less).

On the other hand, the electrode catheter needs to be changed in direction to select a blood vessel which reaches the target region, or needs to bend the tip portion of the catheter shaft largely when the electrode is pressed against the target position. Thus, the catheter shaft constituting the electrode catheter is required to have good kink resistance and torque transmissibility. Further, the catheter shaft needs to have a good pushability.

However, the catheter shaft having a small outside diameter as described above does not have good kink resistance and torque transmissibility because it has low rigidity. Further, the catheter shaft having a small outside diameter has a poor pushability.

Moreover, in a catheter shaft having the single lumen structure like the one constituting the electrode catheter described in Patent Document 1, lead wires extending inside the shaft and a pull wire for pulling operation which moves in an axial direction inside the shaft easily interfere with each other. Consequently, the lead wires may be damaged or broken. Further, the interference between the lead wires and the pull wire occurs more easily in a catheter shaft with a smaller outside diameter.

PRIOR ART DOCUMENT

Patent Document

Patent Document 1: Japanese Patent Application Laid-open No. 2008-245767

SUMMARY OF THE INVENTION

Problems to be Solved by the Invention

The present invention has been made based on the situation as described above.

It is an object of the present invention to provide an electrode catheter having high operability and having good kink resistance, torque transmissibility, and pushability in the entire shaft even when its outside diameter is small.

It is another object of the invention to provide a method for manufacturing an electrode catheter having high operability and having good kink resistance, torque transmissibility, and pushability in the entire shaft even when its outside diameter is small.

Means for Solving the Problem (1) An electrode catheter of the present invention has:
a catheter shaft;
an operating handle connected to a base end side of the catheter shaft;
a connector provided in the operating handle;
a tip electrode attached to a tip of the catheter shaft;
a lead wire having its tip connected to the tip electrode, extending along an axial direction inside the catheter shaft, and having its rear end connected to the connector; and
a wire having its tip fixed to the tip electrode or a tip portion of the catheter shaft, extending along the axial direction inside the catheter shaft, and having its rear end fixed to the operating handle or a base end portion of the catheter shaft,
wherein the catheter shaft has:
a shaft proximal end portion formed of a metal tube having a spiral slit (penetrating slit) formed at least in a tip portion;
a shaft distal end portion formed of a resin tube having a multi-lumen structure coupled to the shaft proximal end portion by inserting its rear end portion into a tip portion of the shaft proximal end portion; and
a resin covering layer covering outer peripheries of the shaft proximal end portion and the rear end portion of the shaft distal end portion, and
wherein the lead wire and the wire extend through different lumens of the shaft distal end portion.

In the electrode catheter of such structure, since the shaft proximal end portion in the catheter shaft is constituted of the metal tube, torque transmissibility and pushability of the shaft proximal end portion can be made quite high as compared to the case where it is constituted of a resin tube.

On the other hand, the shaft distal end portion of this catheter shaft is constituted of the resin tube having the multi-lumen structure. The resin tube having the multi-lumen structure has a higher ratio of resin constituting the tube than the resin tube having a single lumen structure. Therefore, the shaft distal end portion constituted of the resin tube having the multi-lumen structure has sufficiently high operability as compared to one constituted of the resin tube having the single lumen structure.

Thus, even when the outside diameter of the catheter shaft constituting the electrode catheter is small, the entire shaft including the shaft distal end portion has sufficiently high rigidity, and good torque transmissibility and pushability can be exhibited in the entire shaft.

Further, in the above-described electrode catheter, rigidity of the shaft distal end portion constituted of the resin tube is increased by employing the multi-lumen structure, and rigidity of the shaft proximal end portion formed of the metal tube is lowered to a certain degree by forming the spiral slit. Thus, despite that the shaft proximal end portion (metal tube) and the shaft distal end portion (resin tube) are constituted of materials different from each other, rigidity of the catheter shaft does not change excessively between the shaft proximal end portion and the shaft distal end portion.

Thus, since rigidity does not change excessively (or can be changed smoothly) between different materials, it is possible to effectively prevent that stress concentrates between the shaft proximal end portion and the shaft distal end portion and generates a kink when the catheter shaft is bent.

Further, in the above-described electrode catheter, by inserting the rear end portion of the shaft distal end portion into the tip portion of the shaft proximal end portion to couple them, the width of the slit formed in the shaft proximal end portion can be widened easily in a coupling portion. By increasing the slit width in the coupling portion in this manner, rigidity in this coupling portion can be decreased.

Thus, rigidity in the coupling portion can be adjusted to be lower than rigidity of the tip portion of the shaft proximal end portion (portion other than the coupling portion) and higher than rigidity of the shaft distal end portion (portion other than the coupling portion), that is, the rigidity decreases gradually in a direction toward the tip over the entire shaft.

Further, due to that the width of the slit formed in the tip portion of the shaft proximal end portion is widened in the coupling portion to lower rigidity of the coupling portion, generation of kink between the coupling portion and the shaft distal end portion can be prevented.

When the tip portion of the shaft proximal end portion (flexible deformation part of the base part shaft in which the slit is formed) formed of a metal tube is inserted into the shaft distal end portion (tip shaft) formed of a resin tube to couple them, a slit width of the shaft proximal end portion cannot be widened in the coupling portion (that is, rigidity in the coupling portion cannot be lowered), and thus rigidity of the coupling portion becomes highest. In such a case, adjustment to lower the rigidity in the direction toward the tip is not possible.

Further, in the above-described electrode catheter, due to that the resin covering layer covering the outer peripheries of the shaft proximal end portion and the shaft distal end portion is formed, the metal constituting the shaft proximal end portion can be prevented from contacting blood while this electrode catheter is used, and liquid tightness of the shaft proximal end portion in which the slit is formed can be assured.

Moreover, in the electrode catheter as described above, since the lead wire and the wire (pull wire or core wire as will be described later) extend through different lumens of the resin tube constituting the shaft distal end portion, interference between the lead wire and the wire can be avoided in the shaft distal end portion. Further, the wire and the lead wire extending through the different lumens in the shaft distal end portion are difficult to contact (interfere) also in the shaft proximal end portion, and damage or cut of the lead wire due to interference with the wire can thereby be prevented.

(2) In the electrode catheter of the present invention, preferably, a pitch of the slit formed in the shaft proximal end portion narrows sequentially or stepwise in a direction toward a tip.

In the electrode catheter of such structure, rigidity of the shaft proximal end portion can be decreased sequentially or stepwise in the direction toward the tip. Thus, a catheter shaft excelling particularly in operability can be structured.

(3) In the electrode catheter of the present invention, preferably, an outside diameter of the catheter shaft is 1.4 mm or less.

In the electrode catheter having such a catheter shaft with a small outside diameter, it is particularly effective to employ the structure of the catheter shaft according to the present invention (the coupling structure between the shaft proximal end portion constituted of the metal tube in which the spiral slit is formed and the shaft distal end portion constituted of the resin tube having the multi-lumen structure).

(4) Preferably, an area ratio of resin constituting the tube is 60% or more in a transverse sectional view of the shaft distal end portion (resin tube having the multi-lumen structure) of the catheter shaft constituting the electrode catheter of the present invention.

In the resin tube having the multi-lumen structure in which the area ratio of resin constituting the tube is 60% or more (the sum of area ratios of the lumens is 40% or less), the shaft distal end portion with sufficiently high rigidity can be structured.

(5) In the electrode catheter of the present invention, preferably, a width ratio ($W1/W0$) is 1.3 or more, where ($W1$) represents a width of the slit in the shaft proximal end portion in a coupling portion to the shaft distal end portion (portion into which the rear end portion of the shaft distal end portion is inserted), and ($W0$) represents a width of the slit of the shaft proximal end portion in a portion other than the coupling portion.

In the electrode catheter of such structure, due to that the width of the slit in the coupling portion is sufficiently widened, rigidity in the coupling portion can be lowered sufficiently, and generation of kink between the coupling portion and the shaft distal end portion can be securely prevented.

(6) In the electrode catheter of the present invention, preferably, a constituent resin of the shaft distal end portion flows into the slit of the shaft proximal end portion in the coupling portion to the shaft distal end portion, and in particular, the constituent resin of the shaft distal end portion which flowed into the slit of the shaft proximal end portion is fused onto the resin covering layer.

In the electrode catheter of such structure, by an anchor effect (meshing effect) of the slit of the shaft proximal end portion and the resin which flowed therein, the shaft proximal end portion formed of the metal tube and the shaft distal end portion formed of the resin tube can be joined strongly.

(7) In the electrode catheter of above (6), preferably, the resin covering layer is formed by shrinking a heat-shrinkable resin tube in a state that the shaft proximal end portion and the rear end portion of the shaft distal end portion are inserted therein, and a melting point of a heat-shrinkable resin constituting the heat-shrinkable resin tube is higher than a melting point of the resin constituting the shaft distal end portion.

With the electrode catheter of such structure, in a manufacturing step thereof (step of forming the resin covering layer), by heating the heat-shrinkable resin tube in a state that the shaft proximal end portion and the rear end portion of the shaft distal end portion are inserted therein under a temperature condition equal to or higher than a melting point of the resin constituting the shaft distal end portion and lower than the melting point of the heat-shrinkable resin, the heat-shrinkable resin tube shrinks to form the resin covering layer, part of the constituent resin of the resin tube to be the shaft distal end portion melts, and the constituent resin of the resin tube (molten resin) can flow into the slit of the shaft proximal end portion in the coupling portion to the shaft distal end portion.

(8) In the electrode catheter of the present invention, preferably, a rear end of the wire is capable of pulling operation, and the tip of the catheter shaft is deflectable by a pulling operation of the rear end of the wire.

(9) A method of the present invention for manufacturing the electrode catheter of above (7), the method including steps of:

enlarging a diameter of a tip region of the tip portion of the metal tube constituting the shaft proximal end portion and enlarging a width of the slit formed in the tip region;

inserting a rear end region of the rear end portion of the resin tube constituting the shaft distal end portion into the tip region of the metal tube, thereby engaging the shaft proximal end portion and the shaft distal end portion; and inserting the shaft proximal end portion and the rear end portion of the shaft distal end portion, which are engaged, into the heat-shrinkable resin tube, and thereafter heating the heat-shrinkable resin tube under a temperature condition equal to or higher than the melting point of the resin constituting the shaft distal end portion and lower than the melting point of the heat-shrinkable resin to shrink the heat-shrinkable resin tube, to thereby crimp an engaging portion of the shaft proximal end portion and the shaft distal end portion to couple the shaft proximal end portion and the shaft distal end portion, thereby forming the resin covering layer on the outer peripheries of the shaft proximal end portion and the rear end portion of the shaft distal end portion which are coupled.

Effects of the Invention

In an electrode catheter of the present invention, even when an outside diameter of a catheter shaft constituting the electrode catheter is small, the entire shaft including a shaft distal end portion has sufficiently high rigidity, and good kink resistance, torque transmissibility and pushability can be exhibited in the entire shaft.

Further, in a catheter shaft constituting the electrode catheter of the present invention, although the shaft proximal end portion is formed of a metal tube and the shaft distal end portion is formed of a resin tube, rigidity does not change excessively between the shaft proximal end portion and the shaft distal end portion. Thus, generation of kink between the shaft proximal end portion and the shaft distal end portion can be prevented.

Further, in the electrode catheter of the present invention, even when an outside diameter of the catheter shaft constituting the electrode catheter is small, interference between a lead wire and a wire extending inside the shaft can be avoided, and damage or cut of the lead wire due to interference with the wire can be prevented.

By a manufacturing method of the present invention, it is possible to manufacture an electrode catheter provided with a catheter shaft having sufficiently high rigidity and having good kink resistance, torque transmissibility, and pushability in the entire shaft even when its outside diameter is small, in which the shaft proximal end portion and the shaft distal end portion are joined firmly.

BRIEF DESCRIPTION OF DRAWINGS

FIGS. 8A-8B are sectional views for explaining a method for manufacturing the electrode catheter illustrated in FIG. 1.

FIGS. 9A-9B are sectional views for explaining the method for manufacturing the electrode catheter illustrated in FIG. 1.

FIG. 10 is a sectional view (with a partial plan view) illustrating an electrode catheter according to another embodiment of the present invention.

MODE FOR CARRYING OUT THE INVENTION

First Embodiment

Figure 1:
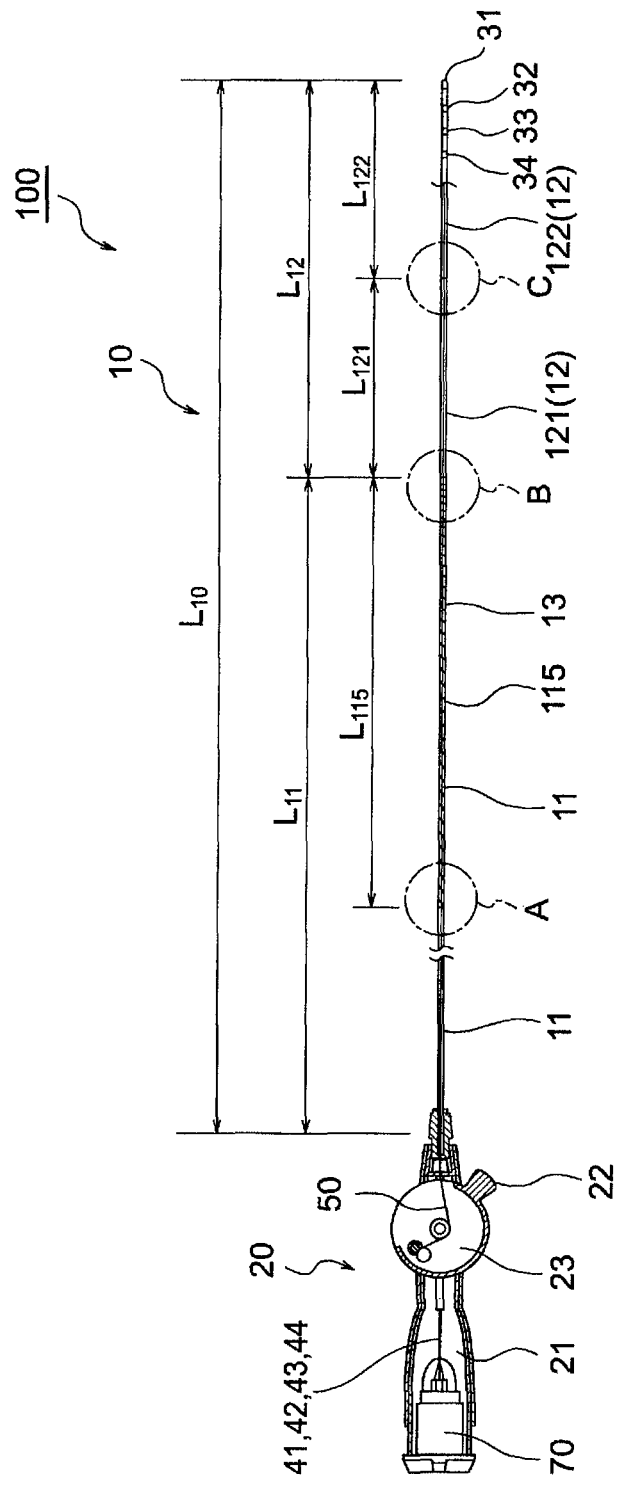
FIG. 1 is a sectional view (with a partial plan view) illustrating an electrode catheter according to one embodiment of the present invention.

An electrode catheter 100 of this embodiment illustrated in FIG. 1 to FIG. 7 is, for example, used for measuring potential in a region of a pulmonary vein of heart, or the like.

This electrode catheter 100 includes a catheter shaft 10, an operating handle 20 connected to a base end side of this catheter shaft 10, a connector 70 attached inside this operating handle 20, a tip electrode 31 attached to a tip of the catheter shaft 10, three ring-shaped electrodes 32, 33, 34 attached to an outer periphery of a tip portion of the catheter shaft 10, four lead wires 41, 42, 43, 44 having respective tips connected to the tip electrode 31 and the ring-shaped electrodes 32, 33, 34, respectively, extending along an axial direction inside, the catheter shaft 10, and having respective rear ends connected to the connector 70, and a pull wire 50 having its tip fixed to the tip electrode 31, extending along the axial direction inside the catheter shaft 10, and having a rear end fixed to a rotation plate 23 of the operating handle 20. The catheter shaft 10 constituting this electrode catheter 100 is constituted of a shaft proximal end portion 11 formed of a metal tube having a spiral slit 115 formed in a tip portion, a shaft distal end portion 12 formed of a resin tube having a multi-lumen structure (first multi-lumen tube 121 and second multi-lumen tube 122) coupled to the shaft proximal end portion 11 by inserting a rear end region of its rear end portion into a tip region of the tip portion of the shaft proximal end portion 11, and a resin covering layer 13 covering outer peripheries of the shaft proximal end portion 11 and the rear end portion of the shaft distal end portion 12. In this electrode catheter 100, the lead wire 41, the lead wires 42, 43, 44, and the pull wire 50 extend through different lumens of the resin tube constituting the shaft distal end portion 12.

The catheter shaft 10 constituting the electrode catheter 100 is constituted of the shaft proximal end portion 11, the shaft distal end portion 12, and the resin covering layer 13.

A length ($L_{10}$) of the catheter shaft 10 is generally 400 mm to 1500 mm, preferably 600 mm to 1200 mm. One preferred example is 1000 mm.

An outside diameter of the catheter shaft 10 is preferably 1.4 mm or less. One preferred example is 0.65 mm. When such a catheter shaft with a small outside diameter is formed only of a resin tube, it is not possible to achieve a catheter shaft having sufficient rigidity, and thus employing the structure of the shaft of this embodiment is particularly effective.

As illustrated in FIG. 1, FIG. 2, FIG. 3, FIG. 5 and FIG. 6, the shaft proximal end portion 11 of the catheter shaft 10 is formed of a metal tube (hypo tube) having a spiral slit 115 formed in a tip portion.

The metal tube constituting the shaft proximal end portion 11 has a single lumen structure, and examples of the metal constituting the shaft proximal end portion 11 include stainless steel, NiTi, and β-titanium.

The shaft proximal end portion 11 formed of a metal tube has much higher rigidity as compared to the case where it is formed of a resin tube, and thus can exhibit excellent kink resistance, torque transmissibility and pushability even when the outside diameter of the shaft is small.

In the tip portion of the metal tube constituting the shaft proximal end portion 11, the spiral slit 115 is formed. This slit 115 is a penetrating slit reaching an inner peripheral surface from an outer peripheral surface of the metal tube. Thus, when the electrode catheter 100 is manufactured as will be described later, the width of the slit 115 can be enlarged in an axial direction of the shaft, and also the outside diameter of the portion where the slit 115 is formed can also be enlarged.

By forming the spiral slit 115, rigidity of the metal tube in the portion where the spiral slit exists is lowered to a certain degree, giving flexibility thereto. Thus, the shaft proximal end portion 11 can be formed so that it has both intrinsically high rigidity (excellent kink resistance and pushability) of the metal tube and flexibility in the tip portion.

In the tip portion of the metal tube constituting the shaft proximal end portion 11, a pitch of the spiral slit 115 is formed to be sequentially narrower in a direction toward the tip.

Thus, rigidity of the tip portion of the shaft proximal end portion 11 can be decreased sequentially (smoothly) toward the tip, by which the catheter shaft 10 excelling particularly in kink resistance can be formed.

A length ($L_{11}$) of the shaft proximal end portion 11 is generally 300 mm to 1000 mm, preferably 400 mm to 950 mm. One preferred example is 880 mm.

A length ($L_{115}$) of the tip portion of the metal tube in which the spiral slit 115 is formed is generally 40 mm to 200 mm, preferably 50 mm to 160 mm. One preferred example is 130 mm.

Figure 2:
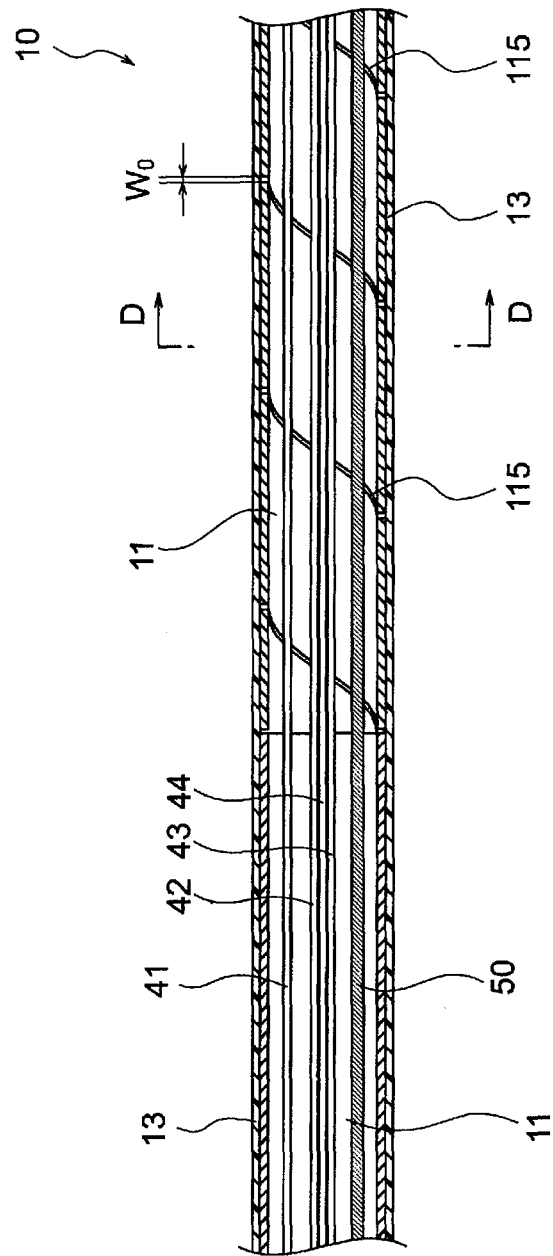
FIG. 2 is a sectional view (detailed sectional view of part A of FIG. 1) illustrating a shaft proximal end portion of the catheter shaft constituting the electrode catheter illustrated in FIG. 1.
Figure 3:
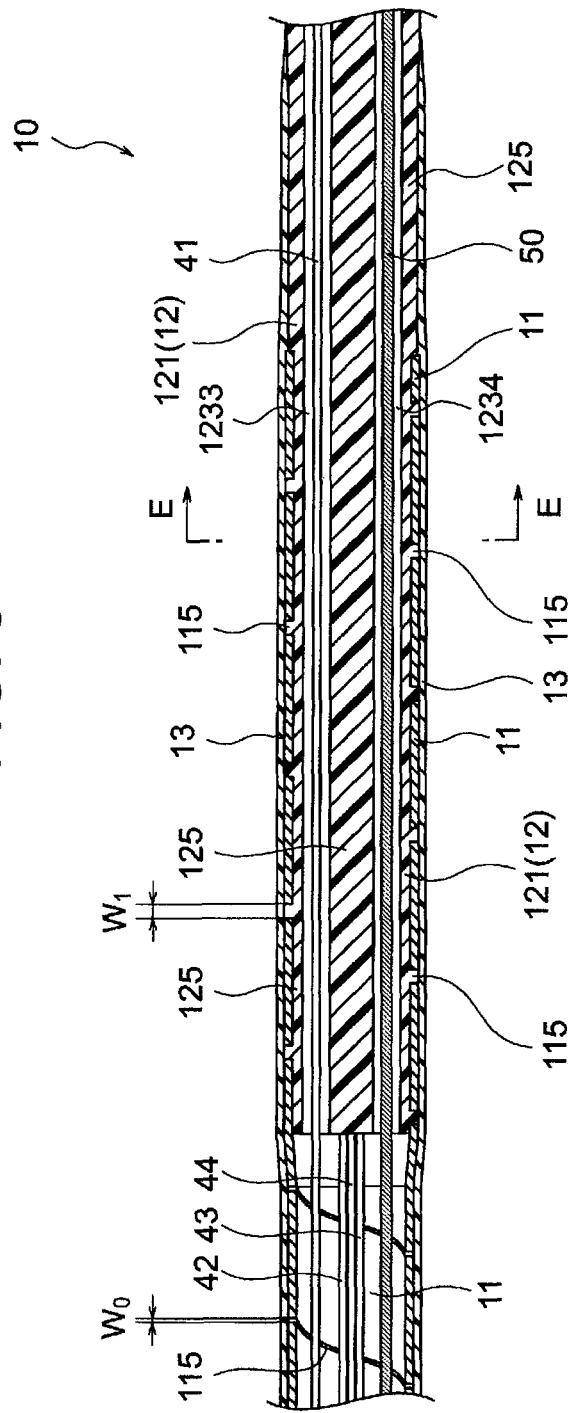
FIG. 3 is a sectional view (detailed sectional view of part B of FIG. 1) illustrating a coupling portion between the shaft proximal end portion and a shaft distal end portion of the catheter shaft constituting the electrode catheter illustrated in FIG. 1.
Figure 4:
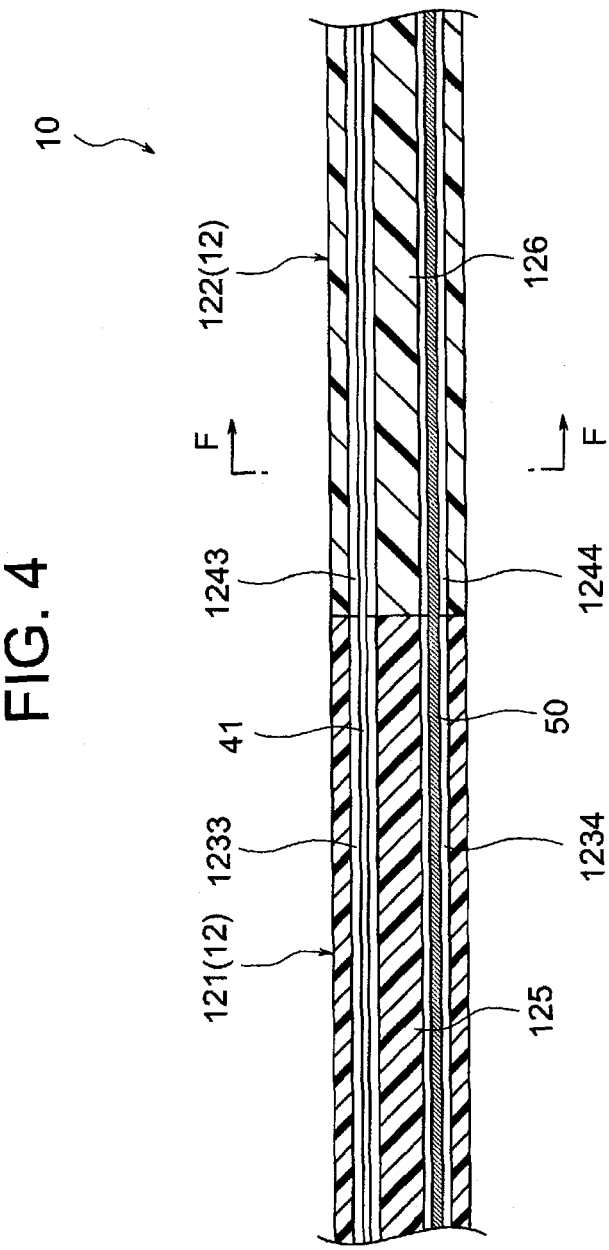
FIG. 4 is a sectional view (detailed sectional view of part C of FIG. 1) illustrating the shaft distal end portion of the catheter shaft constituting the electrode catheter illustrated in FIG. 1.

A width (denoted by ($W_0$) in FIG. 2 and FIG. 3) of the slit 115 in the shaft proximal end portion 11 (portion other than a coupling portion to the shaft distal end portion 12) is generally 0.005 mm to 0.100 mm. One preferred example is 0.01 mm.

A method for forming the slit 115 in the metal tube is not particularly limited, and laser beam machining, electric discharge machining, chemical etching, cutting, or the like can be employed.

As illustrated in FIG. 1, FIG. 3, FIG. 4, FIG. 6 and FIG. 7, the shaft distal end portion 12 of the catheter shaft 10 is constituted of an insulating resin tube having a multi-lumen structure.

The resin tube constituting the shaft distal end portion 12 is formed by fusing two multi-lumen tubes having different hardness (first multi-lumen tube 121 and second multi-lumen tube 122).

Note that in the present invention, the shaft distal end portion may be constituted of three or more multi-lumen tubes having different hardness.

Figure 6:
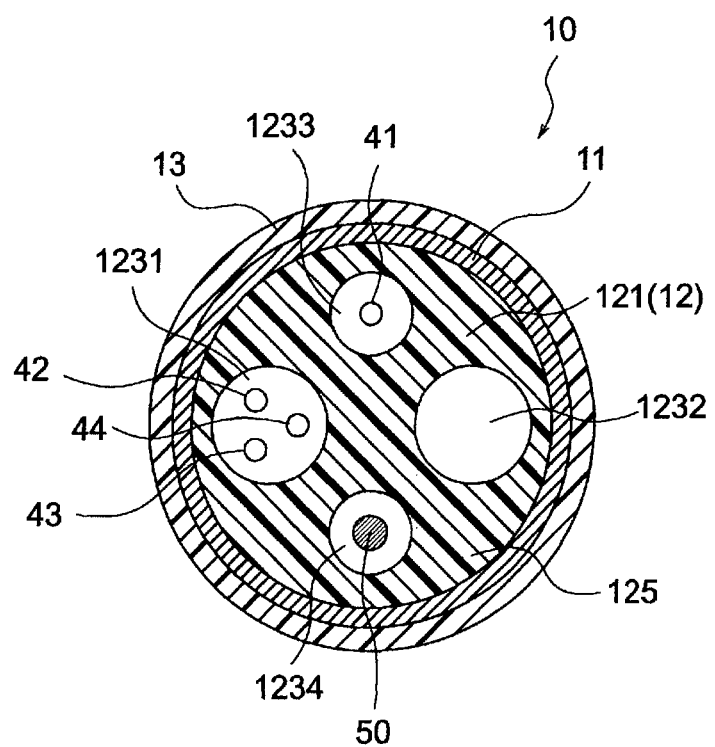
FIG. 6 is a transverse sectional view (E-E sectional view) of the coupling portion illustrated in FIG. 3.

As illustrated in FIG. 6, four lumens (first lumen 1231, second lumen 1232, third lumen 1233, fourth lumen 1234) are formed in the first multi-lumen tube 121 constituting the rear end portion of the shaft distal end portion 12. In this view, 125 denotes a resin constituting the first multi-lumen tube 121 by sectioning the lumens 1231 to 1234.

Figure 7:
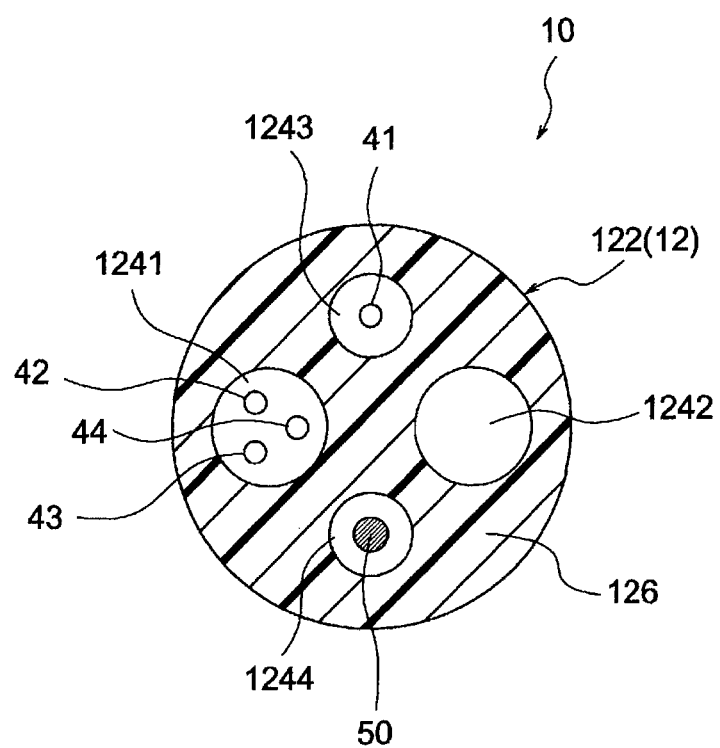
FIG. 7 is a transverse sectional view (F-F sectional view) of the shaft distal end portion illustrated in FIG. 4.
Figure 11:
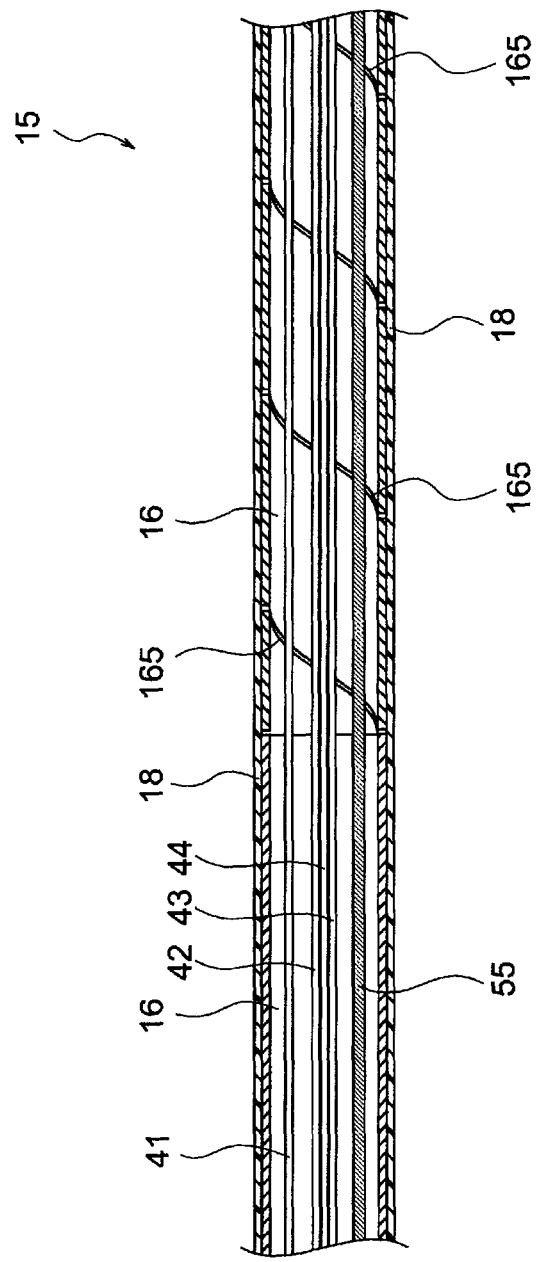
FIG. 11 is a sectional view (detailed sectional view of part G of FIG. 10) illustrating a shaft proximal end portion of a catheter shaft constituting the electrode catheter illustrated in FIG. 10.

As illustrated in FIG. 7, four lumens (first lumen 1241, second lumen 1242, third lumen 1243, fourth lumen 1244) are formed in the second multi-lumen tube 122 constituting the tip portion of the shaft distal end portion 12. In this view, 126 denotes a resin constituting the second multi-lumen tube 122 by sectioning the lumens 1241 to 1244.

An example of the resin (resin 125, resin 126) constituting the resin tubes (first multi-lumen tube 121, second multi-lumen tube 122) is a polyether block amide copolymer (PEBAX(registered trademark)).

As illustrated in FIG. 6 and FIG. 7, the first multi-lumen tube 121 and the second multi-lumen tube 122 have the same multi-lumen structure (transverse sectional shape). That is, the first lumen 1231, the second lumen 1232, the third lumen 1233 and the fourth lumen 1234 formed in the first multi-lumen tube 121 communicate with the first lumen 1241, the second lumen 1242, the third lumen 1243 and the fourth lumen 1244, respectively, formed in the second multi-lumen tube 122.

The constituent resin 125 of the first multi-lumen tube 121 has higher hardness than the constituent resin 126 of the second multi-lumen tube 122.

Here, hardness of the resin 125 (measured with a D-type hardness meter) is 55D to 72D, and one preferred example is 68D. On the other hand, hardness of the resin 126 is 25D to 50D, and one preferred example is 40D.

A length ($L_{12}$) of the shaft distal end portion 12 is generally 30 mm to 300 mm, preferably 50 mm to 200 mm. One preferred example is 120 mm.

Further, a length ($L_{121}$) of the first multi-lumen tube 121 is generally 15 to 150 mm, preferably 25 mm to 100 mm. One preferred example is 60 mm.

Further, a length ($L_{122}$) of the second multi-lumen tube 122 is generally 15 to 150 mm, preferably 25 mm to 100 mm. One preferred example is 60 mm.

Similarly to the resin tube constituting the shaft distal end portion 12, the resin tube having the multi-lumen structure has a higher ratio of resin constituting the tube than the resin tube having the single lumen structure.

Here, in a transverse sectional view of the shaft distal end portion 12 as illustrated in FIG. 6 and FIG. 7, an area ratio of resin (resin 125 and resin 126) constituting the resin tube (the first multi-lumen tube 121 and the second multi-lumen tube 122) is preferably 60% or more, and one preferred example is 66%.

Thus, the resin tube having the multi-lumen structure with a high proportion of resin can constitute the shaft distal end portion 12 with sufficiently high rigidity.

Further, by employing the multi-lumen structure, rigidity of the shaft distal end portion 12 (resin tube) is increased, and by forming the slit 115, rigidity of the shaft proximal end portion 11 (metal tube) is decreased to a certain degree. Thus, despite that the shaft proximal end portion 11 and the shaft distal end portion 12 are constituted of materials different from each other, rigidity of the catheter shaft 10 between them will not change abruptly, but rather, the rigidity can be decreased (lowered) smoothly in the direction toward the tip.

Thus, when the tip portion of the catheter shaft 100 is bent, it is possible to effectively prevent the concentration of stress between the shaft proximal end portion 11 and the shaft distal end portion 12 thereby avoiding a kink.

As illustrated in FIG. 3, the shaft distal end portion 12 and the shaft proximal end portion 11 are coupled by inserting (engaging) the rear end region of the rear end portion (first multi-lumen tube 121) of the former into the tip region of the tip portion of the latter.

By inserting the rear end region of the rear end portion of the shaft distal end portion 12 into the tip region of the tip portion of the shaft proximal end portion 11 to couple them, the width of the slit 115 formed in the tip portion of the shaft proximal end portion 11 can be widened easily in a coupling portion (tip region of the tip portion).

As illustrated in FIG. 3, the width ($W_1$) of the slit 115 of the shaft proximal end portion 11 in the coupling portion to the shaft distal end portion 12 (first multi-lumen tube 121) is actually wider compared to the width ($W_0$) of the slit 115 of the shaft proximal end portion 11 in the portion other than the coupling portion.

Here, preferably, the width ($W_1$) of the slit 115 in the coupling portion is preferably equal to or more than 1.3 times the width ($W_0$) of the slit 115 in the portion other than the coupling portion, and one preferred example is 5.0 times.

Thus, due to that the width ($W_1$) of the slit 115 of the shaft proximal end portion 11 in the coupling portion to the shaft distal end portion 12 is sufficiently wider than the width ($W_0$) of the slit 115 in the portion other than the coupling portion, rigidity in the coupling portion can be lower than rigidity of the tip portion (portion where the width of the slit 115 is formed to be the normal width ($W_0$)) of the shaft proximal end portion 11 and higher than rigidity of the shaft distal end portion 12. That is, the coupling portion can become an intermediate rigid portion, with which the catheter shaft 10 having rigidity gradually decreasing in the direction toward the tip in the entire shaft can be formed.

Further, due to that the width ($W_1$) of the slit 115 of the shaft proximal end portion 11 in the coupling portion to the shaft distal end portion 12 is sufficiently wider than the width ($W_0$) of the slit 115 in the portion other than the coupling portion, rigidity of the coupling portion can be decreased sufficiently. Consequently, generation of kink between the coupling portion and the shaft distal end portion 12 can be securely prevented.

Moreover, in this catheter shaft 10, part of the resin constituting the shaft distal end portion 12 (constituent resin 125 of the first multi-lumen tube 121) flows into the slit 155 in the coupling portion to the shaft distal end portion 12, and the resin 125 which flowed into the slit 115 contacts the resin covering layer 13 and fuses onto the resin covering layer 13.

Thus, by an anchor effect (meshing effect) of the slit 115 of the shaft proximal end portion 11 and the constituent resin 125 of the shaft distal end portion 12 which flowed into this slit 115 as well as a fusing effect between the resin 125 which flowed into the slit 115 and the resin covering layer 13, the shaft proximal end portion 11 formed of the metal tube and the shaft distal end portion 12 formed of the resin tube can be joined strongly.

Incidentally, as a dilation catheter used for percutaneous transluminal coronary angioplasty (PTCA), there exists a dilation catheter which has a catheter shaft having a shaft proximal end portion formed of a metal tube in which a spiral slit is formed and a shaft distal end portion formed of a resin tube, which are coupled by inserting (engaging) a tip portion of the shaft proximal end portion into the shaft distal end portion.

Accordingly, in an electrode catheter having a catheter shaft with a small outside diameter, it is conceivable to form a catheter shaft by, similarly to the above dilation catheter, coupling (engaging) a shaft proximal end portion formed of a metal tube in which a spiral slit is formed and a shaft distal end portion formed of a resin tube.

In such an electrode catheter, sufficiently high rigidity can be assured in the shaft proximal end portion formed of a metal tube.

However, in such an electrode catheter, rigidity of the shaft distal end portion formed of a resin tube is still low, and the kink resistance and the pushability of the shaft distal end portion cannot be improved.

Further, in order to make a catheter shaft having good kink resistance, it is important to change (lower) rigidity gradually in the direction toward the tip. However, the rigidity changes excessively between the shaft proximal end portion formed of a metal tube and the shaft distal end portion formed of a resin tube, and thus stress during bending concentrates therebetween, making it easy to kink.

Further, in a catheter shaft made by inserting the tip portion of the shaft proximal end portion in the shaft distal end portion similarly to the above dilation catheter to couple them, the coupling portion (engaging portion) of the shaft proximal end portion and the shaft distal end portion is a portion having highest rigidity.

Thus, in this coupling portion, it is not possible to gradually decrease the rigidity of the shaft in the direction toward the tip, and moreover, a kink is easily taken place between this coupling portion and the shaft distal end portion (in the portion other than the coupling portion).

Further, when the catheter shaft is constituted of the shaft proximal end portion formed of a metal tube and the shaft distal end portion formed of a resin tube similarly to the above-described dilation catheter, it is difficult to join the metal tube and the resin tube with high strength.

As illustrated in FIG. 2 and FIG. 3, the resin covering layer 13 constituting the catheter shaft 10 covers the outer peripheries of the shaft proximal end portion 11 and the rear end portion of the shaft distal end portion 12.

The resin covering layer 13 is formed on an outer peripheral surface over the entire length of the shaft proximal end portion 11 and on an outer peripheral surface in the rear end portion of the shaft distal end portion 12 (first multi-lumen tube 121).

The resin covering layer 13 has a thickness of, for example, 5 μm to 50 μm, preferably 10 μm to 30 μm.

The resin covering layer 13 is formed by shrinking a heat-shrinkable resin tube in a state that the shaft proximal end portion 11 and the rear end portion of the shaft distal end portion 12 are inserted therein.

An example of the heat-shrinkable resin tube for forming the resin covering layer 13 is a polyether block amide copolymer resin (PEBAX(registered trademark)).

Due to that the catheter shaft 10 is structured by forming the resin covering layer 13 covering the outer peripheries of the shaft proximal end portion 11 and the rear end portion of the shaft distal end portion 12, the metal constituting the shaft proximal end portion 11 can be prevented from contacting blood while the electrode catheter 100 is used, and liquid tightness of the shaft proximal end portion 11 in which the slit 115 is formed can be assured.

The heat-shrinkable resin constituting the heat-shrinkable resin tube forming the resin covering layer 13 has a higher melting point than the resin constituting the shaft distal end portion 12 (the resin 125 constituting the first multi-lumen tube 121).

Thus, in a method for manufacturing the electrode catheter (formation step of the resin covering layer) which will be described later, by heating the heat-shrinkable resin tube (shaft forming resin) in a state that the shaft proximal end portion 11 and the rear end portion of the shaft distal end portion 12 are inserted therein under a temperature condition equal to or higher than a melting point of the constituent resin (resin 125) of the resin tube to be the shaft distal end portion 12 and lower than the melting point of the heat-shrinkable resin, part of the constituent resin (resin 125) of the resin tube melts, and this molten resin can flow into the slit 115 formed in the shaft proximal end portion 11 in the coupling portion to the shaft distal end portion 12.

As illustrated in FIG. 1, the operating handle 20 is connected to the base end side of the catheter shaft 10.

The operating handle 20 constituting the electrode catheter 100 has a handle main body 21 and the rotation plate 23 having a knob 22, and a connector 70 is attached inside the operating handle 20.

The tip electrode 31 is fixed to the tip of the catheter shaft 10.

Examples of constituent material of the tip electrode 31 include metals with good heat conductivity such as aluminum, copper, stainless steel, gold, and platinum. Preferably, the tip electrode 31 is constituted of platinum or the like for giving a good imaging property with respect to X rays.

The outside diameter of the tip electrode 31 is not particularly limited, but is preferred to be approximately the same as the outside diameter of the catheter shaft 10.

The three ring-shaped electrodes 32, 33, 34 are attached to the outer periphery of the tip portion of the catheter shaft 10.

Examples of constituent material of the ring-shaped electrodes 32, 33, 34 are the metals exemplified as one constituting the tip electrode 31.

The outside diameters of the ring-shaped electrodes 32, 33, 34 are also not particularly limited, but are preferred to be approximately the same as the outside diameter of the catheter shaft 10.

Inside the catheter shaft 10, the four lead wires 41, 42, 43, 44 having respective tips connected to the tip electrode 31 and the ring-shaped electrodes 32, 33, 34, respectively, extend along the axial direction. Further, inside the catheter shaft 10, the pull wire 50 having its tip connected to the inside of the tip electrode 31 extends along the axial direction.

As illustrated in FIG. 6 and FIG. 7, the three lead wires 42, 43, 44 connected respectively to the ring-shaped electrodes 32, 33, 34 extend in the first lumen (lumen 1231 and lumen 1241) of the resin tube (first multi-lumen tube 121 and second multi-lumen tube 122) constituting the shaft distal end portion 12.

Respective rear ends of these lead wires 42, 43, 44 are connected to the connector 70 attached inside the operating handle 20, as illustrated in FIG. 1.

Further, the lead wire 41 connected to the tip electrode 31 extends through the third lumen (lumen 1233 and lumen 1243) of the resin tube constituting the shaft distal end portion 12, and a rear end of this lead wire 41 is connected to the connector 70 attached inside the operating handle 20, similarly to the lead wires 42, 43, 44.

Further, the pull wire 50 fixed to the tip electrode 31 extends through the fourth lumen (lumen 1234 and lumen 1244) of the resin tube constituting the shaft distal end portion 12.

A tip of the pull wire 50 is fixed strongly with a solder filled inside the tip electrode 31.

On the other hand, a rear end of the pull wire 50 is fixed to the rotation plate 23 of the operating handle 20 as illustrated in FIG. 1.

Thus, disengagement or the like of the tip electrode 31 can be securely prevented. Moreover, the pull wire 50 can be pulled by rotary operating the rotation plate 23, thereby bending the tip portion (shaft distal end portion 12) of the catheter shaft 10 to deflect (swing) the tip.

Here, examples of the constituent material of the pull wire 50 include metal materials such as stainless steel and Ni—Ti-based superelastic alloy, non-conductive materials with high strength, and the like.

Note that in this embodiment, the lead wires and the pull wire do not extend through the second lumen (lumen 1232 and lumen 1242) of the shaft distal end portion 12.

As described above, since the three lead wires 42, 43, 44 extend through the first lumen (1231, 1241), the lead wire 41 extends through the third lumen (1233, 1243), and the pull wire 50 extends through the fourth lumen (1234, 1244), interference (contact) between the lead wires 41, 42, 43, 44 and the pull wire 50 in the shaft distal end portion 12 can be avoided.

Figure 5:
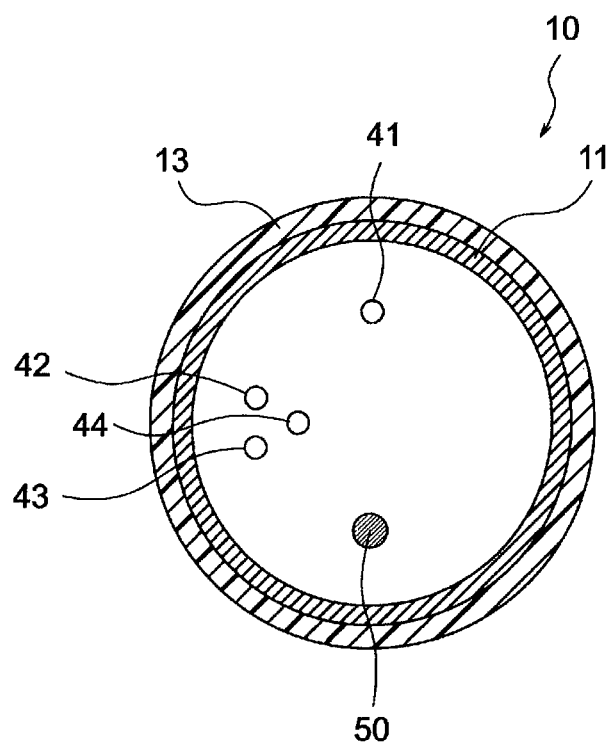
FIG. 5 is a transverse sectional view (D-D sectional view) of the shaft proximal end portion illustrated in FIG. 2.

Moreover, the pull wire 50 and the lead wires 41, 42, 43, 44 extending through the different lumens in the shaft distal end portion 12 are, as illustrated in FIG. 5, separated and difficult to contact (interfere) each other inside the shaft proximal end portion 11.

Consequently, during a tip deflecting operation of the electrode catheter 100 of this embodiment, the pull wire 50 moving in the axial direction can be prevented from damaging (for example, scratching) or cutting the lead wires 41, 42, 43, 44.

The electrode catheter 100 of this embodiment can be manufactured preferably by a method including the following steps (1) to (5).

(1) as illustrated in FIG. 8 (FIG. 8A), a metal tube 110 having the spiral slit 115 formed in a tip portion is prepared.

Here, illustrating an example of the metal tube 110, a stainless tube can be used which has an outside diameter ($D_0$) of 0.65 mm and an inside diameter ($d_0$) of 0.55 mm, with a width ($W_0$) of the slit 115 being 0.01 mm.

(2) as illustrated in FIG. 8 (FIG. 8B), a tip region (opening vicinity region) of the tip portion of the metal tube 110 is enlarged in diameter, and a width of the slit 115 in the tip region is enlarged.

Here, the length of the enlarged tip region is approximately 4 mm.

The enlarged tip region of the metal tube 110 has, for example, an outside diameter ($D_1$) of 0.76 mm, an inside diameter ($d_1$) of 0.66 mm, with a width ($W_1$) of the slit 115 being 0.05 mm [($W_1/W_0$)=5).

(3) as illustrated in FIG. 9 (FIG. 9A), a rear end portion of the resin tube 120 having the multi-lumen structure is inserted into the enlarged tip region of the metal tube 110, thereby engaging the metal tube 110 and the resin tube 120.

Here, an outside diameter of the rear end portion of the resin tube 120 is of a degree that it can be inserted into the tip region of the metal tube 110 and that it will not be pulled off easily after insertion (for example, approximately 0.65 mm). The rear end portion of the resin tube 120 may be subjected to cutting as necessary to have such an outside diameter.

(4) as illustrated in FIG. 9 (FIG. 9B), the metal tube 110 and the rear end portion of the resin tube 120 which are engaged are inserted into the heat-shrinkable resin tube 130.

Here, the metal tube 110 is, over its entire length, inserted into the heat-shrinkable resin tube 130.

(5) the shaft forming material in a state illustrated in FIG. 9B is heated at a temperature equal to or higher than the melting point of the resin constituting the resin tube 120 and lower than the melting point of the heat-shrinkable resin constituting the heat-shrinkable resin tube 130, thereby shrinking the heat-shrinkable resin tube 130.

By contraction of the heat-shrinkable resin tube 130, the tip region of the metal tube 110 (engaging portion of the metal tube 110 and the resin tube 120) is crimped, and the tip region of the metal tube 110 is shrunk to have approximately the same diameter as the outside diameter ($D_0$) before it is enlarged in diameter. The metal tube 110 and the resin tube 120 are thereby coupled, and a resin covering layer made by shrinking the heat-shrinkable resin tube 130 is formed on the outer periphery of the metal tube 110 and the outer periphery of the rear end portion of the resin tube 120.

At this time, in the engaging portion of the metal tube 110 and the resin tube 120, part of the constituent resin of the resin tube 120 melts and flows into the enlarged slit 115 in the metal tube 110, and the resin in a molten state which flowed into the slit 115 contacts the inner peripheral surface of the shrunk heat-shrinkable resin tube 130 and fuses thereon. Thus, the above-described anchor effect (meshing effect) and the fusing effect can be exhibited.

Note that in the slit 115 in the tip region of the metal tube 110 (coupling portion to the resin tube 120), by the constituent resin of the resin tube 120 which flowed therein, the width ($W_1$) enlarged in above step (2) is maintained.

In the steps as described above, it is possible to manufacture the catheter shaft 10 having the coupling portion as illustrated in FIG. 3, that is, the catheter shaft 10 in which the shaft proximal end portion 11 formed of the metal tube (110) and the shaft distal end portion 12 formed of the resin tube (120) are coupled by inserting the rear end region of the rear end portion of the shaft distal end portion 12 into the tip region of the tip portion of the shaft proximal end portion 11, and the outer peripheries of the shaft proximal end portion 11 and the rear end portion of the shaft distal end portion 12 are covered by the resin covering layer 13 formed by shrinking the heat-shrinkable resin tube 130.

In the electrode catheter 100 of this embodiment, even when the outside diameter of the catheter shaft 10 constituting the electrode catheter is small, the entire shaft including the shaft distal end portion 12 has sufficiently high rigidity, and good kink resistance, torque transmissibility and pushability can be exhibited in its entirety.

Further, in the catheter shaft 10, although the shaft proximal end portion 11 is formed of the metal tube and the shaft distal end portion 12 is formed of the resin tube, rigidity does not change excessively between the shaft proximal end portion 11 and the shaft distal end portion 12. Thus, generation of kink between the shaft proximal end portion 11 and the shaft distal end portion 12 can be prevented.

Further, by part of the constituent resin 125 of the shaft distal end portion 12 which flowed into the slit 115 of the shaft proximal end portion 11 in the coupling portion to the shaft distal end portion 12, the shaft distal end portion 12 and the shaft proximal end portion 11 constituted of different materials can be joined firmly.

Further, due to that a width ratio ($W_1/W_0$) is 1.3 or more as noted above, the coupling portion of the shaft proximal end portion 11 and the shaft distal end portion 12 can become an intermediate rigid portion, with which the catheter shaft 10 having rigidity gradually decreasing in the direction toward the tip can be formed. Moreover, occurrence of kink between this coupling portion and the shaft distal end portion 12 can be securely prevented.

Further, interference between the lead wires 41, 42, 43, 44 and the pull wire 50 extending inside the catheter shaft 10 can be avoided, and damage or cut of the lead wires due to interference with the pull wire 50 can be prevented.

Second Embodiment

An electrode catheter 150 illustrated in FIG. 10 to FIG. 13 is used for measuring potential in a portion of a pulmonary vein of heart, or the like, and has a catheter shaft 15, an operating handle 25 connected to a base end side of this catheter shaft 15, a connector (not illustrated) attached inside this operating handle 25, a tip electrode 31 attached to a tip of the catheter shaft 15, seven ring-shaped electrodes 32, 33, 34, 35, 36, 37, 38 attached to an outer periphery of a tip portion of the catheter shaft 15, eight lead wires 41, 42, 43, 44, 45, 46, 47, 48 having respective tips connected to the tip electrode 31 and the ring-shaped electrodes 32 to 38, respectively, extending along an axial direction inside the catheter shaft 15, and having respective rear ends connected to the connector, and a core wire 55 having its tip fixed to the tip electrode 31, extending along the axial direction inside the catheter shaft 15, and having a rear end fixed to a base end portion of the catheter shaft 15. The catheter shaft 15 constituting this electrode catheter 150 is constituted of a shaft proximal end portion 16 formed of a metal tube having a spiral slit 165 formed in a tip portion, a shaft distal end portion 17 formed of a resin tube having a multi-lumen structure (first multi-lumen tube 171 and second multi-lumen tube 172) coupled to the shaft proximal end portion 16 by inserting a rear end region of its rear end portion into a tip region of the tip portion of the shaft proximal end portion 16, and a resin covering layer 18 covering outer peripheries of the shaft proximal end portion 16 and the rear end portion of the shaft distal end portion 17. In this electrode catheter 150, the lead wire 41, the lead wires 42, 43, 44, the lead wires 45, 46, 47, 48, and the core wire 55 extend through different lumens of the resin tube constituting the shaft distal end portion 17.

The catheter shaft 15 constituting the electrode catheter 150 is constituted of the shaft proximal end portion 16, the shaft distal end portion 17, and the resin covering layer 18.

A length ($L_{15}$) of the catheter shaft 15 is generally 600 mm to 1700 mm, preferably 700 mm to 1500 mm. One preferred example is 1300 mm.

An outside diameter of the catheter shaft 15 is preferably 1.4 mm or less.

The shaft proximal end portion 16 of the catheter shaft 15 is formed of the metal tube having the spiral slit 165 formed in the tip portion, which is substantially similar to the shaft proximal end portion 11 according to the first embodiment, thus achieves operations and effects equivalent to those of this shaft proximal end portion 11.

A length ($L_{16}$) of the shaft proximal end portion 16 is generally 500 mm to 1500 mm, preferably 600 mm to 1200 mm. One preferred example is 1030 mm.

A length ($L_{165}$) of the tip portion of the metal tube in which the spiral slit 165 is formed is generally 50 mm to 200 mm, preferably 100 mm to 150 mm. One preferred example is 130 mm.

Figure 12:
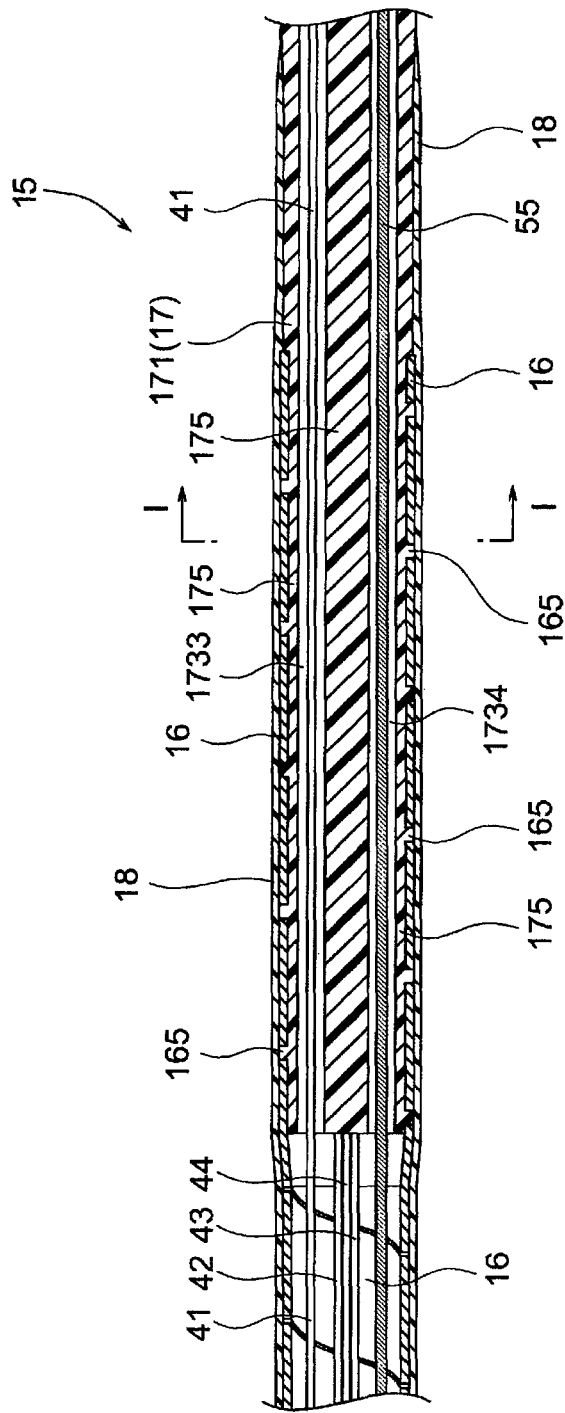
FIG. 12 is a sectional view (detailed sectional view of part H of FIG. 10) illustrating a coupling portion between the shaft proximal end portion and a shaft distal end portion of the catheter shaft constituting the electrode catheter illustrated in FIG. 10.
Figure 13:
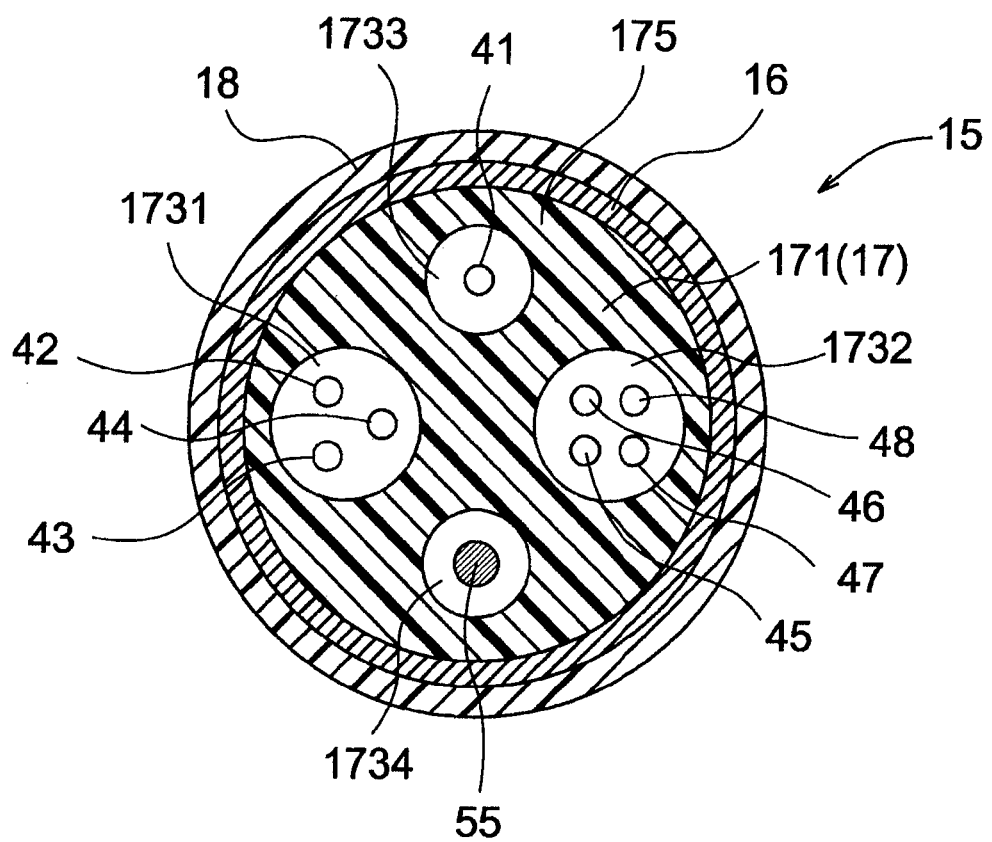
FIG. 13 is a transverse sectional view (I-I sectional view) of the coupling portion illustrated in FIG. 12.

As illustrated in FIG. 10, FIG. 12 and FIG. 13, the shaft distal end portion 17 of the catheter shaft 15 is constituted of an insulating resin tube having a multi-lumen structure, which is similar to the shaft distal end portion 12 according to the first embodiment, thus achieves operations and effects equivalent to those of this shaft distal end portion 12.

The resin tube constituting the shaft distal end portion 17 is formed by fusing two multi-lumen tubes having different hardness (first multi-lumen tube 171 and second multi-lumen tube 172).

As illustrated in FIG. 13, in the first multi-lumen tube 171 constituting the rear end portion of the shaft distal end portion 17, four lumens (first lumen 1731, second lumen 1732, third lumen 1733, fourth lumen 1734) are formed. In this view, 175 denotes a resin constituting the first multi-lumen tube 171 by sectioning the lumens 1731 to 1734.

The second multi-lumen tube 172 constituting a tip portion of the shaft distal end portion 17 has the same multi-lumen structure (transverse sectional shape) as the first multi-lumen tube 171.

A length ($L_{17}$) of the shaft distal end portion 17 is generally 100 mm to 400 mm, preferably 150 mm to 300 mm. One preferred example is 270 mm.

Further, a length ($L_{171}$) of the first multi-lumen tube 171 is generally 80 mm to 300 mm, preferably 100 mm to 250 mm. One preferred example is 220 mm.

Further, a length ($L_{172}$) of the second multi-lumen tube 172 is generally 15 mm to 80 mm, preferably 20 mm to 60 mm. One preferred example is 50 mm.

As illustrated in FIG. 12, the shaft distal end portion 17 and the shaft proximal end portion 16 are coupled by inserting (engaging) the rear end region of the rear end portion (first multi-lumen tube 171) of the former into the tip region of the tip portion of the latter.

Moreover, in this catheter shaft 15, part of the resin constituting the shaft distal end portion 17 (constituent resin 175 of the first multi-lumen tube 171) flows into the slit 165 in the coupling portion to the shaft distal end portion 17, and the resin 175 which flowed into the slit 165 contacts the resin covering layer 18 and fuses onto the resin covering layer 18.

As illustrated in FIG. 12 and FIG. 13, the resin covering layer 18 constituting the catheter shaft 15 covers the outer peripheries of the shaft proximal end portion 16 and the rear end portion of the shaft distal end portion 17.

The resin covering layer 18 is formed on an outer peripheral surface over the entire length of the shaft proximal end portion 16 and on an outer peripheral surface in the rear end portion of the shaft distal end portion 17 (first multi-lumen tube 171).

The resin covering layer 18 is structured similarly to the resin covering layer 13 according to the first embodiment, and exhibits operation and effect similar to those of this resin covering layer 13.

As illustrated in FIG. 10, although the catheter shaft 15 constituting the electrode catheter 150 has a straight shape, the shaft distal end portion 17 in a state that no external force is applied may have a specific curve shape. A catheter shaft having (memorizing) such a curve shape easily changes when an external force is applied (for example, passing the catheter shaft through a sheath), but when the external force is removed, it can return to the memorized curve shape.

The operating handle 25 is connected to the base end side of the catheter shaft 15.

This operating handle 25 is a handle for rotary operating the catheter shaft 15 around a shaft. A connecter (omitted from illustration) is attached inside the operating handle 25.

The tip electrode 31 is fixed to the tip of the catheter shaft 15.

Further, the seven ring-shaped electrodes 32, 33, 34, 35, 36, 37, 38 are attached to the outer periphery of the tip portion of the catheter shaft 15.

Inside the catheter shaft 15, the eight lead wires having respective tips connected to the tip electrode 31 and the ring-shaped electrodes 32 to 38, respectively, extend along the axial direction. Further, inside the catheter shaft 15, a core wire 55 having its tip connected to the tip electrode 31 extends along the axial direction.

As illustrated in FIG. 13, the three lead wires 42, 43, 44 connected to the ring-shaped electrodes 32, 33, 34, respectively, extend through the first lumen (the first lumen 1731 of the first multi-lumen tube 171 and the first lumen of the second multi-lumen tube 172 communicating therewith) of the resin tube constituting the shaft distal end portion 17.

Respective rear ends of these lead wires 42, 43, 44 are connected to the connecter attached inside the operating handle 25.

Further, the lead wires 45, 46, 47, 48 connected to the ring-shaped electrodes 35, 36, 37, 38 extend through the second lumen (the second lumen 1732 of the first multi-lumen tube 171 and the second lumen of the second multi-lumen tube 172 communicating therewith) of the resin tube constituting the shaft distal end portion 17.

Respective rear ends of these lead wires 45, 46, 47, 48 are connected to the connector attached in the operating handle 25, similarly to the lead wires 42, 43, 44.

Further, the lead wire 41 connected to the tip electrode 31 extends through the third lumen (the third lumen 1733 of the first multi-lumen tube 171 and the third lumen of the second multi-lumen tube 172 communicating therewith) of the resin tube constituting the shaft distal end portion 17. A rear end of this lead wire 41 is connected to the connector attached inside the operating handle 25, similarly to the lead wires 42 to 48.

Further, the core wire 55 fixed to the tip electrode 31 extends through the fourth lumen (the fourth lumen 1734 of the first multi-lumen tube 171 and the fourth lumen of the second multi-lumen tube 172 communicating therewith) of the resin tube constituting the shaft distal end portion 17.

A tip of the core wire 55 is fixed strongly with a solder filled inside the tip electrode 31. On the other hand, a rear end of the core wire 55 is fixed with an adhesive or the like to the base end portion of the catheter shaft 15 (shaft proximal end portion 16). Thus, disengagement or the like of the tip electrode 31 can be securely prevented.

The electrode catheter 150 of this embodiment is not one in which the tip of the catheter shaft 15 is deflected by pulling the core wire 55 (catheter capable of tip deflecting operation). However, even in an electrode catheter which does not perform a tip deflecting operation, the shaft shape changes corresponding to the shape of a blood vessel (sheath), and thus means for preventing interference between the core wire 55 and the lead wires 41 to 48 are needed.

In this embodiment, the lead wires 42, 43, 44 extend through the first lumen, the lead wires 45, 46, 47, 48 extend through the second lumen, the lead wire 41 extends through the third lumen, and the core wire 55 extends through the fourth lumen. Thus, interference between the lead wires 41 to 48 and the core wire 55 in the shaft distal end portion 17 can be avoided.

Further, the core wire 55 and the lead wires 41 to 48 extended in the different lumens in the shaft distal end portion 17 are separated and difficult to contact (interfere) each other inside the shaft proximal end portion 16. Consequently, damage or cut of the lead wires 41 to 48 can be prevented due to interference with the core wire 55.

In the electrode catheter 150 of this embodiment, even when the outside diameter of the catheter shaft 15 constituting the electrode catheter is small, the entire shaft including the shaft distal end portion 17 has sufficiently high rigidity, and good kink resistance, torque transmissibility and pushability can be exhibited in its entirety.

Further, rigidity does not change excessively between the shaft proximal end portion 16 and the shaft distal end portion 17. Thus, generation of kink between the shaft proximal end portion 16 and the shaft distal end portion 17 can be prevented.

Further, by part of the constituent resin 175 of the shaft distal end portion 17 which flowed into the slit 165 of the shaft proximal end portion 16 in the coupling portion to the shaft distal end portion 17, the shaft distal end portion 17 and the shaft proximal end portion 16 constituted of different materials can be joined firmly.

100 electrode catheter
10 catheter shaft
11 shaft proximal end portion
110 metal tube
115 slit
12 shaft distal end portion
120 resin tube
121 first multi-lumen tube
122 second multi-lumen tube
1231, 1241 first lumen
1232, 1242 second lumen
1233, 1243 third lumen
1234, 1244 fourth lumen
125, 126 constituent resin of multi-lumen tube
13 resin covering layer
130 heat-shrinkable resin tube
20 operating handle
21 handle main body
22 knob
23 rotation plate
31 tip electrode
32 to 34 ring-shaped electrode
41 to 44 lead wire
23 rotation plate
50 pull wire
70 connector
150 electrode catheter
15 catheter shaft
16 shaft proximal end portion
165 slit
17 shaft distal end portion
171 first multi-lumen tube 171
172 second multi-lumen tube 172
1731 first lumen
1732 second lumen 1732
1733 third lumen 1733
1734 fourth lumen 1734
175 constituent resin of multi-lumen tube
18 resin covering layer
25 operating handle
35 to 38 ring-shaped electrode
45 to 48 lead wire
55 core wire

The invention claimed is:

1. An electrode catheter, comprising:
a catheter shaft;
an operating handle connected to a base end side of the catheter shaft;
a connector provided in the operating handle;
a tip electrode attached to a tip of the catheter shaft;
a lead wire having its tip connected to the tip electrode, extending along an axial direction inside the catheter shaft, and having its rear end connected to the connector; and
a wire having its tip fixed to the tip electrode or a tip portion of the catheter shaft, extending along the axial direction inside the catheter shaft, and having its rear end fixed to the operating handle or a base end portion of the catheter shaft,
wherein the catheter shaft comprises:
a shaft proximal end portion formed of a metal tube having a spiral slit formed at least in a tip portion;
a shaft distal end portion formed of a resin tube having a multi-lumen structure coupled to the shaft proximal end portion by inserting a rear end region of its rear end portion into a tip region of the tip portion of the shaft proximal end portion; and
a resin covering layer covering outer peripheries of the shaft proximal end portion and the rear end portion of the shaft distal end portion, and
wherein the lead wire and the wire extend through different lumens of the shaft distal end portion,
wherein a constituent resin of the shaft distal end portion flows into the slit of the shaft proximal end portion in a coupling portion to the shaft distal end portion,
wherein the resin covering layer is formed by shrinking a heat-shrinkable resin tube into which the shaft proximal end portion and the rear end portion of the shaft distal end portion are inserted, and a melting point of a heat-shrinkable resin constituting the heat-shrinkable resin tube is higher than a melting point of the constituent resin of the shaft distal end portion, and
wherein a width ratio (W1/W0) is 1.3 or more, where (W1) represents a width of the slit in the shaft proximal end portion in the coupling portion between the shaft proximal end portion and the shaft distal end portion, and (W0) represents a width of the slit of the shaft proximal end portion in a portion other than the coupling portion.

2. The electrode catheter according to claim 1,
wherein a pitch of the slit formed in the shaft proximal end portion narrows sequentially or stepwise in a direction toward a tip.

3. The electrode catheter according to claim 1,
wherein an outside diameter of the catheter shaft is 1.4 mm or less.

4. The electrode catheter according to claim 1,
wherein an area ratio of resin constituting the tube in the resin tube forming the shaft distal end portion is 60% or more in a transverse sectional view.

5. The electrode catheter according to claim 1,
wherein the rear end of the wire is capable of a pulling operation, and the tip of the catheter shaft is deflectable by the pulling operation of the rear end of the wire.

6. A method for manufacturing the electrode catheter according to claim 1, the method comprising the following steps of:
enlarging a diameter of the tip region of the tip portion of the metal tube constituting the shaft proximal end portion and enlarging a width of the slit formed in the tip region;

inserting the rear end region of the rear end portion of the resin tube constituting the shaft distal end portion into the tip region of the metal tube, thereby engaging the shaft proximal end portion and the shaft distal end portion; and
inserting the shaft proximal end portion and the rear end portion of the shaft distal end portion, which are engaged, into the heat-shrinkable resin tube, and thereafter heating the heat-shrinkable resin tube under a temperature condition equal to or more than the melting point of the constituent resin of the shaft distal end portion and less than the melting point of the heat-shrinkable resin to shrink the heat-shrinkable resin tube, to thereby crimp an engaging portion of the shaft proximal end portion and the shaft distal end portion to couple the shaft proximal end portion and the shaft distal end portion, thereby forming the resin covering layer on the outer peripheries of the shaft proximal end portion and the rear end portion of the shaft distal end portion which are coupled.

* * * * *